United States Patent
Kurrus et al.

(10) Patent No.: US 9,440,045 B2
(45) Date of Patent: Sep. 13, 2016

(54) CURVED TIP HEMODIALYSIS CATHETER

(71) Applicant: Cook Medical Technologies LLC, Bloomington, IN (US)

(72) Inventors: Michael R. Kurrus, Ellettsville, IN (US); Tyson Rugenstein, Camby, IN (US); Meridith Cavett, Dexter, MI (US)

(73) Assignee: Cook Medical Technologies LLC, Bloomington, IN (US)

( * ) Notice: Subject to any disclaimer, the term of this patent is extended or adjusted under 35 U.S.C. 154(b) by 112 days.

(21) Appl. No.: 13/799,012

(22) Filed: Mar. 13, 2013

(65) Prior Publication Data

US 2014/0221898 A1 Aug. 7, 2014

Related U.S. Application Data

(60) Provisional application No. 61/759,576, filed on Feb. 1, 2013.

(51) Int. Cl.
*A61M 37/00* (2006.01)
*A61M 25/00* (2006.01)
*A61M 1/36* (2006.01)

(52) U.S. Cl.
CPC ....... *A61M 25/003* (2013.01); *A61M 25/0068* (2013.01); *A61M 1/3661* (2014.02); *A61M 25/001* (2013.01); *A61M 25/007* (2013.01); *A61M 2025/0031* (2013.01); *A61M 2025/0037* (2013.01)

(58) Field of Classification Search
CPC ......... A61M 25/007; A61M 25/0068; A61M 2025/0031; A61M 2025/0037; A61M 25/003; A61M 25/0029; A61M 1/3661; A61M 1/6653

USPC ......................................................... 604/6.16
See application file for complete search history.

(56) References Cited

U.S. PATENT DOCUMENTS

| | | | |
|---|---|---|---|
| 4,619,643 A | 10/1986 | Bai | |
| 5,209,742 A * | 5/1993 | Venema et al. | 604/507 |
| 6,508,790 B1 | 1/2003 | Lawrence | |
| 6,517,529 B1 | 2/2003 | Quinn | |
| 6,709,414 B2 | 3/2004 | Weitzel et al. | |
| 6,997,894 B2 * | 2/2006 | Caresio | 604/6.16 |
| 7,276,043 B2 | 10/2007 | Heath et al. | |
| 7,569,029 B2 | 8/2009 | Clark | |
| 7,695,450 B1 | 4/2010 | Twardowski et al. | |
| 7,763,196 B2 | 7/2010 | Goebel et al. | |
| 7,896,861 B2 | 3/2011 | McFerran et al. | |
| 8,029,495 B2 | 10/2011 | Pyles | |
| 8,057,424 B2 | 11/2011 | Patterson et al. | |
| 8,066,660 B2 | 11/2011 | Gregersen et al. | |
| 2002/0188166 A1 * | 12/2002 | Viole | A61M 1/3653 600/16 |
| 2009/0054826 A1 * | 2/2009 | Hoffa | 604/6.16 |
| 2011/0213291 A1 * | 9/2011 | Quinn | 604/6.16 |

* cited by examiner

*Primary Examiner* — Leslie Deak
*Assistant Examiner* — Ariana Zimbouski
(74) *Attorney, Agent, or Firm* — Woodard Emhardt Moriarty McNett & Henry LLP

(57) ABSTRACT

A hemodialysis catheter for use within a vein of a patient includes a catheter body having a proximal end when positioned within and relative to the vein. The catheter body defines an arterial lumen and a venous lumen. The catheter body is shaped with a curved tip which has a distal end. The venous lumen is truncated at a location between the proximal end of the catheter body and the distal end of the curved tip. The truncated location of the venous lumen defines an out-flow opening. The distal end of the curved tip defines an in-flow opening which corresponds to the arterial lumen. The vein has a blood flow direction and the in-flow opening faces the blood flow direction.

14 Claims, 3 Drawing Sheets

CURVED TIP HEMODIALYSIS CATHETER

CROSS-REFERENCE TO RELATED APPLICATIONS

This application claims the benefit of U.S. Provisional Application No. 61/759,576, filed Feb. 1, 2013, which is incorporated herein in its entirety.

BACKGROUND

Multi-lumen catheters are "suitable", based on conventional wisdom and usage, for use in conjunction with hemodialysis applications. Having two (2) or more lumens means two (2) or more separate fluid flow passages. For hemodialysis applications, one (1) lumen handles the flow of blood being removed for processing by a dialysis machine and the other lumen handles the blood being returned to the patient. The use of a multi-lumen catheter, normally a dual lumen catheter, allows the contaminated blood ("bad" blood) and the cleansed blood ("good" blood) to be kept separate as part of an effective dialysis procedure.

Current hemodialysis catheters are used to filter blood in the superior vena cava (SVC). When using a two-lumen hemodialysis catheter, the arterial lumen is used to aspirate blood which is routed to the dialysis machine for cleansing. The venous lumen is used to eject the filtered blood (good blood) into the SVC and then to the heart and lungs, and to the rest of the body of the patient.

Traditionally, the venous (out-flow) lumen is always the distal lumen and the arterial (in-flow) lumen is always the proximal lumen. This is done to prevent recirculation, where previously filtered and newly ejected blood is sucked back in and re-filtered by the dialysis machine. Depending on the catheter tip design and placement, the proximal arterial opening can suck the SVC wall next to it, occluding the opening, lowering the flow rate, and preventing dialysis from taking place. Various prior art hemodialysis catheters have sideports to allow the in-flow of blood from multiple openings. However, this arrangement prevents the use of heparin (or other anti-coagulants) from being used as a "lock". With these prior art constructions, heparin can leak out of the sideports leaving anything distal to the sideport unprotected. As used herein, a heparin "lock" is when the catheter is flushed with heparin and then clamped off between uses, so that the normal inside volume of the catheter is occupied thus preventing thrombus from forming. Various (prior art) medical journal articles point to hemodialysis sideports being a cause of thrombosis and fibrin sheath formation, thus lowering flow rates and making a catheter essentially non-functional.

A solution to one (1) or more of these prior art issues is provided by the exemplary embodiment of the present disclosure. A curved tip hemodialysis catheter is disclosed wherein the curved construction functions, in part, as a type of reinforcement against any appreciable movement of the SVC wall which might be sufficient to occlude a flow opening of the catheter. This issue has been mentioned above and is discussed in the context of the proximal arterial opening where the SVC wall can be sucked into an occluding position over at least a part or portion of that opening.

The use herein of "curved tip" refers to the distal portion of the catheter and not merely to the distal end. The "tip" refers to that distal portion or length which is sufficient to form a curved, part-circular shape, as described in greater detail herein.

The size, shape and material resiliency of the curved tip portion provides support against the inner surface of the SVC wall. This curved tip portion functions to physically spread apart the SVC, similar in this regard to a vena cava filter. The level or degree of physical support or physical reinforcement against the SVC wall which is provided by the curved tip portion of the disclosed catheter prevents the SVC vein wall from being sucked around the flow opening of the arterial (in-flow) lumen of the catheter. The exemplary embodiment negates any "need" for possible corrective measures such as the addition of sideports and in so doing eliminates the risk of end hole thrombus. One (1) result expected from the exemplary embodiment, as contrasted to prior art structures which have the discussed "issues", is an increased flow rate and a decrease in the total time to dialyze a patient.

One (1) consequence of shaping a hemodialysis catheter with a curved tip is to reverse or switch the traditional functionality of the two (2) lumens of the catheter. Traditionally, the proximal lumen is the arterial lumen for in-flow and the distal lumen is the venous lumen for out-flow. While the two (2) lumens of the catheter essentially run side-by-side, the use of "proximal" and "distal" refers to the relative locations of the defined flow openings for each of those two (2) lumens. In the exemplary embodiment, considering simply the elongated form of the catheter prior to being formed with a curved tip, these two (2) flow openings are reversed. In this regard, it will be seen that in the exemplary embodiment the flow opening which is proximal corresponds to the venous lumen and the flow opening which is distal corresponds with the arterial lumen. It will also be seen that surrounding the flow opening of the arterial lumen, there are no sideports.

The addition of a tip curvature of at least approximately 180 degrees provides a structure wherein the flow openings of the two (2) lumens are separated further. As disclosed herein, relative to the exemplary embodiment, the venous lumen and its flow opening point in a direction which is essentially opposite to the opening direction of the flow opening of the arterial lumen. The result of this construction and structural relationship is a minimal risk or likelihood of blood recirculation. The directions and orientations associated with the exemplary embodiment allow the arterial (in-flow) lumen to directly capture blood from the natural flow pattern, rather than sucking the blood around the edges of the catheter. The exemplary embodiment causes less shearing of the red blood cells due to edge-flow patterns and therefore, less hemolysis.

SUMMARY

A hemodialysis catheter for use within a vein of a patient includes a catheter body having a proximal end when positioned within and relative to the vein. The catheter body defines an arterial lumen and a venous lumen. The catheter body is shaped with a curved tip which has a distal end. The venous lumen is truncated at a location between the proximal end of the catheter body and the distal end of the curved tip. The truncated location of the venous lumen defines an out-flow opening. The distal end of the curved tip defines an in-flow opening which corresponds to the arterial lumen. The vein has a blood flow direction and the in-flow opening faces the blood flow direction.

A hemodialysis catheter for use within a vein of a patient is disclosed and includes a catheter body having an elongate form with a proximal end and a distal end. The catheter body has a length dimension extending between the proximal end and the distal end. Further, the catheter body defines an arterial lumen and a venous lumen. The arterial lumen defines an in-flow opening and the venous lumen defines an out-flow opening. Relative to the length dimension, the out-flow opening is proximal relative to the in-flow opening which is distal relative to the catheter body. The catheter body includes a curved tip which includes the distal end. The curved tip has a shape which positions the in-flow opening upstream relative to the out-flow opening based upon a blood flow direction in the vein.

A method of reinforcing a vein in order to prevent occluding a flow opening of a hemodialysis catheter due to an in-flow suction force is disclosed. The method includes the steps of providing a multi-lumen hemodialysis catheter which includes a first lumen with a distal in-flow opening and a second lumen with a proximal out-flow opening. A subsequent step is the forming of a curved tip at a distal end of the hemodialysis catheter. A still further step is inserting the curved tip into a vein which has a blood flow direction such that the in-flow opening is upstream from the out-flow opening. The curved tip providing a reinforcement structure against vein wall movement into an occluding position over the in-flow opening.

DESCRIPTION OF THE SELECTED EMBODIMENTS

Figure 1:
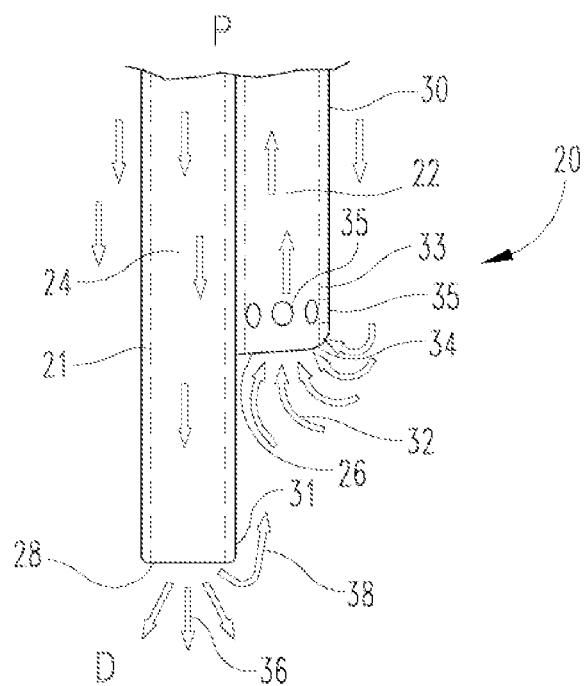
FIG. 1 is a partial, diagrammatic view of a prior art hemodialysis catheter, showing the prior art flow directions.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figure 2:
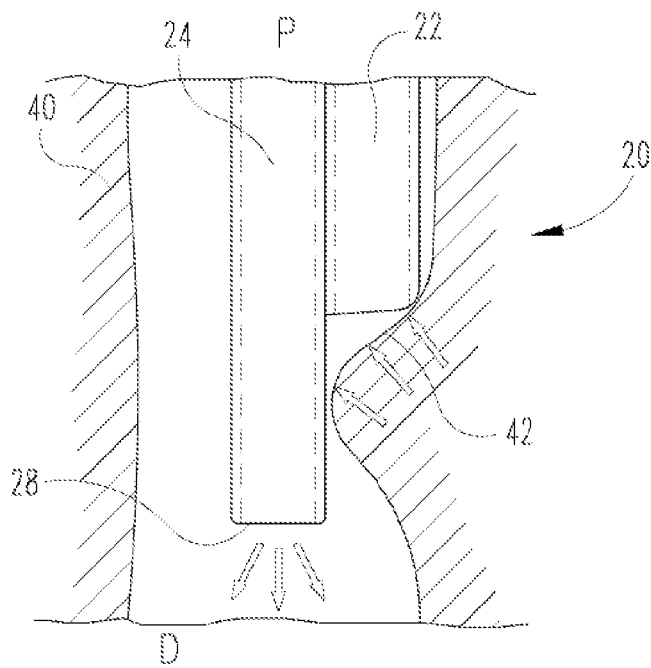
FIG. 2 is a partial, diagrammatic view of the FIG. 1 hemodialysis catheter as positioned in a SVC vein.

Referring to FIGS. 1 and 2, the tip of a prior art hemodialysis catheter is illustrated. Hemodialysis catheter 20 is representative of traditional prior art structures wherein the catheter 20 includes a catheter body 21 defining two (2) lumens 22 and 24 each with a corresponding flow opening 26 and 28, respectively. In the elongated form which is illustrated in FIGS. 1 and 2, the letter P denotes the proximal end of the hemodialysis catheter and the letter D denotes the distal end of the hemodialysis catheter. Consistent with the current state of the prior art, lumen 22 is the arterial lumen which is constructed and arranged to suck in "bad" blood from the patient via flow opening 26. Lumen 24 is the venous lumen which is constructed and arranged to deliver an outflow of "good" blood back to the patient via flow opening 28. The catheter portion which is illustrated in FIG. 1 constitutes the tip 30 of catheter 20 and tip 30 is located at the distal end (D) of catheter 20 based on the convention adopted for this disclosure.

In terms of the relative positions of the two (2) lumens 22 and 24 and of their corresponding flow openings 26 and 28, the prior art arterial lumen 22 is the proximal lumen of the two (2) lumens. The prior art venous lumen 24 is the distal lumen of the two (2) lumens. The convention adopted for proximal (P) and distal (D) is applicable not only to the locations on the actual catheter, but also the locations relative to the SVC vein of the patient. As shown by arrows 32, a portion of the circulating blood of the patient is drawn into flow opening 26 and to do so the blood flow must make something similar to a "U-turn" and actually flow over the edge 34 which in part defines flow opening 26.

Considering the structure of catheter 20 and its elongated configuration, in order to provide flow opening 26, the portion of catheter 20 which defines arterial lumen 22 is truncated at a location which is upstream from the distal end 31. This upstream truncation of arterial lumen 22 provides the exposed end which defines flow opening 26. This structural arrangement is why the arterial flow opening 26 is proximal and the venous flow opening 28 is distal, as between the two (2) and as positioned in the SVC.

The distal portion 33 of arterial lumen 22 defines a plurality of sideports 35 which open into the interior of arterial lumen 22. Blood also flows into lumen 22 by turning and flowing in through sideports 35. While not as sharp a turn as the full U-turn into opening 26, there is still blood flow across the sideport edges. One (1) reason to include sideports 35 in these prior art structures is due to the positioning of opening 26. The referenced "U-turn" causes the blood flow to slow in order to make the turn and this reduces the flow volume. The sideports 35 are intended to supplement the total flow volume of the blood being diverted to the hemodialysis machine via the arterial lumen 22. One (1) issue with the addition and use of sideports 35 has been discussed in the Background. That discussion is repeated here for added emphasis.

Various prior art hemodialysis catheters have sideports to allow the in-flow of blood from multiple openings. However, this arrangement prevents the use of heparin (or other anti-coagulants) from being used as a "lock". With these prior art constructions, heparin can leak out of the sideports leaving anything distal to the sideport unprotected. As used herein, a heparin "lock" is when the catheter is flushed with heparin and then clamped off between uses, so that the normal inside volume of the catheter is occupied thus preventing thrombus from forming. Various (prior art) medical journal articles point to hemodialysis sideports being a cause of thrombosis and fibrin sheath formation, thus lowering flow rates and making a catheter essentially non-functional.

The flow of blood over edge 34 and over the edges of the sideports 35 has the effect of increasing the shear forces on the red blood cells. One (1) adverse consequence of the shearing of the red blood cells is hemolysis which is the rupturing of the red blood cells and the release of their contents (hemoglobin). This is a negative effect or consequence relative to the overall hemodialysis procedure. Eliminating this U-turn over edge 34 and its associated shearing of the red blood cells would constitute an improvement to the catheter tip construction and to the hemodialysis procedure.

With continued reference to FIG. 1, arrows 36 represent the out-flow of blood which has been processed by the hemodialysis machine. Briefly, the hemodialysis machine receives a flow of blood from the patient and removes unwanted waste products from the blood before returning the blood to the patient. Dialysate is the fluid which helps to remove the unwanted waste products.

As shown by arrow 38, it is possible, given the positions and proximity of flow openings 26 and 28, for some of the re-entering flow of blood via flow opening 28 to be sucked in (again) by flow opening 26. In view of the blood which needs to be processed and typical time for a patient to complete a procedure, re-processing of "good" blood is a redundancy which is unnecessary and inefficient.

Referring now to FIG. 2, another issue with current prior art hemodialysis catheters is illustrated in conjunction with catheter 20. In the prior art arrangement of FIG. 2, catheter 20 is positioned in a vein 40 and in the exemplary embodiment, this vein 40 is the superior vena cava (SVC). As the hemodialysis procedure is being conducted, a suction force, via lumen 22, which is intended to suck in "bad" blood via opening 26 and sideports 35, is exerted on the SVC wall. If that suction force on the SVC wall is strong enough, it will actually pull a portion 42 of the SVC wall which is next to opening 26 into an occluding position over at least a portion of opening 26. Such an occluding condition, whether partial or total, results in lowering the flow rate of the blood which is drawn in via opening 26. This reduction in the flow rate may reach a level such that dialysis cannot take place.

Figure 3:
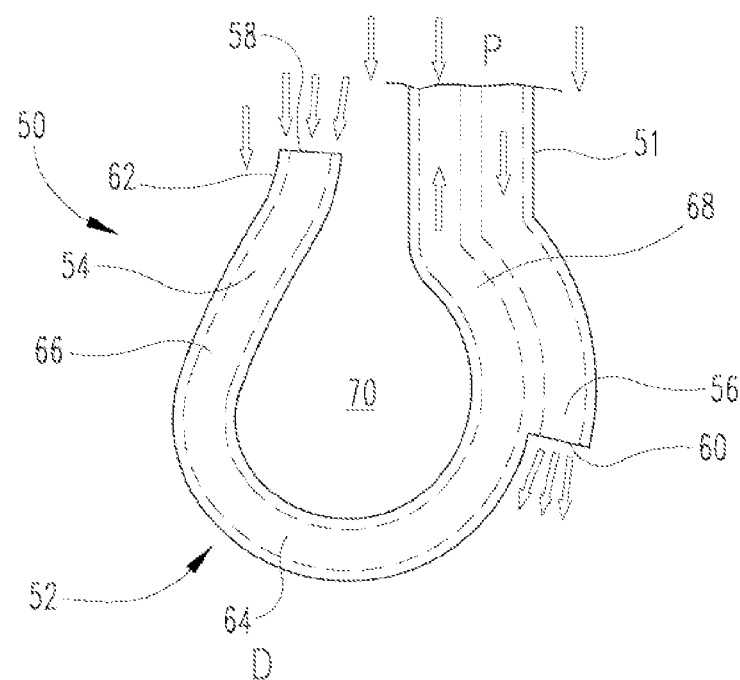
FIG. 3 is a partial, diagrammatic view, of a hemodialysis catheter according to the exemplary embodiment.

With the prior art issues in mind, the structure of the exemplary embodiment will now be described in the context of and with reference to FIGS. 3 and 4. Disclosed is a hemodialysis catheter 50 which includes an initially elongate catheter body 51 wherein its distal portion has been shaped into a curved tip 52. Catheter 50 is a two-lumen catheter for this description, but other, additional lumens could be included as a part of catheter 50 if other functions need to be performed or if other flows, either in or out, might be desired. Curved tip 52 can assume a variety of sizes and shapes, so long as its basic structural characteristics are preserved and maintained. Those basic structural characteristics will be described in conjunction with the exemplary embodiment. It is to be understood that elongate catheter body 51 has a proximal end and a distal end as it exists prior to being shaped with curved tip 52. However, the references to proximal (P) and distal (D) remain the same in terms of blood flow and that would be the "upstream" location of the SVC.

Catheter body 51 defines arterial lumen 54 for handling the in-flow of "bad" blood and venous lumen 56 for providing the out-flow of "good" blood. Arterial lumen 54 defines flow opening 58 which, in the "curved tip" form which is illustrated, opens in an upstream direction, directly in line with the entering flow direction of the existing blood flow in the SVC. This existing flow is in a downstream direction consistent with the FIG. 4 illustration. This blood flow alignment between the natural flow (i.e. the existing flow) within the patient and the upwardly opening direction of flow opening 58, precludes the need for any "U-turns" and precludes the need for any sideports. Venous lumen 56 defines flow opening 60 which opens outwardly with an exiting flow direction which is substantially the same as the blood flow direction through the SVC. Essentially, the blood flow direction which enters opening 58 is substantially the same as the blood flow direction which is exiting from flow opening 60.

Considering the structure of catheter 50 and its elongated catheter body 51 configuration, prior to being formed with the illustrated "curved tip" 52, the portion of catheter 50 which defines the venous lumen 56 is truncated at a location which is upstream from the distal end 62. This truncation forms flow opening 60. The distal end 62 defines flow opening 58 and, prior to forming the curved tip 52, flow opening 58 is directed in a downward direction. As indicated above, the proximal end of catheter 50 is denoted by the letter P. It is to be understood that the catheter body 51 begins as an elongated form wherein the proximal/distal locations of the arterial (in-flow) flow opening and the venous (out-flow) flow opening are reversed from their relative positions in the prior art.

As noted, the relative positions of flow openings 58 and 60, as part of hemodialysis catheter 50, are reversed or switched from the relative positions of the prior art catheters. Considering the basic structure of each catheter 20 and 50, not its shaping or arrangement in the SVC, it will be seen that for catheter 20, flow opening 26 is proximal and flow opening 28 is distal. As for catheter 50, flow opening 58 is distal and flow opening 60 is proximal. As such, the location of the arterial flow opening along the length of the catheter and the location of the venous flow opening (of catheter 50) are reversed from their counterpart flow openings in prior art catheter 20. When catheter 50 is shaped into its curved tip form (see FIGS. 3 and 4), the distal end 62 is brought upwardly such that flow opening 58 becomes proximal, as shaped and positioned within the SVC, and flow opening 60 is directed in a downstream direction into the center of SVC. The curved tip 52 has the shape of a loop or semi-circle or hook, none of which are fully closed. There is as part of curved tip 52 a curved distal section 64 with flow opening 60 on the upstream side of section 64 and with flow opening 58 on the downstream side of section 64.

As explained herein, one (1) function of curved tip 52 is to spread apart the SVC, similar to a vena cava filter, so that the vein wall cannot be sucked inwardly around or over the flow opening of the arterial (in-flow) lumen. This aspect eliminates or negates the "need" for sideports and precludes in-flow thrombus. In turn there is an increase in the flow rate and a decrease in the total time to dialyze a patient. There are several ways to fabricate or form curved tip 52. The method selected for the exemplary embodiment is to heat-set the polymer material of catheter 50 with a forming wire. It is known that urethanes can be heat set in different shapes with forming wires at temperatures between 150 degrees F. and 300 degrees F. The curve is preferably at least approximately 180 degrees, but can be greater.

Lumen 54 extends through catheter 50 to the distal end 62. Lumen 56 extends through a portion of catheter 50 and ends at the truncated location which defines flow opening 60. The curved tip form of catheter 50 creates greater longitudinal separation between the two (2) flow openings 58 and 60. This greater separation lessens the risk or likelihood that "good" blood exiting from flow opening 60 would be sucked in by flow opening 58 and re-circulated. While the increased distance of separation is the primary factor in preventing a likelihood of re-circulation, the orientation of the arterial flow opening 58 is a contributing factor. As noted, the arterial flow opening 58 is open upwardly in the direction of the approaching blood flow such that the suction into flow opening 58 is aligned with that blood flow without the need for any U-turns and without the need for any sideports.

The curved tip structure of the exemplary embodiment of catheter 50 and the improvement in the aligned flow into flow opening 58 results in essentially no sucking in of blood around any edges and this means less shearing of the red blood cells and therefore less hemolysis with the present disclosure. The location, direction and positioning of flow opening 58, due to the curved tip configuration, allows the arterial (in-flow) lumen 54 to directly capture blood from the body's natural flow pattern.

Figure 4:
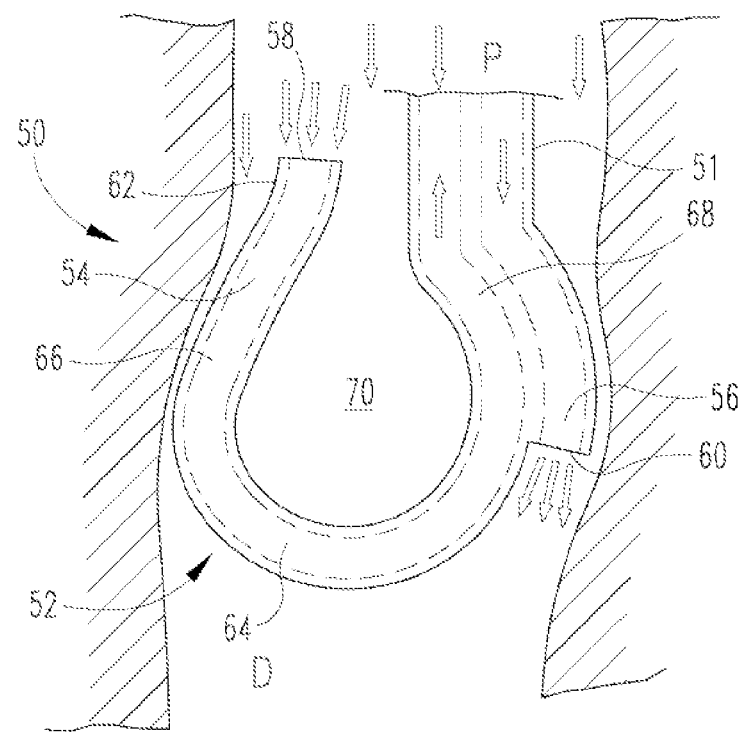
FIG. 4 is a partial, diagrammatic view of the FIG. 3 hemodialysis catheter as positioned in a SVC vein.

With further reference to FIG. 4, the curved tip catheter 50 is illustrated as it would be positioned in the SVC. The arrows show the in-flow and out-flow of blood relative to catheter 50. Based on the illustration of curved tip 52, focusing now on downstream section 66, it will be seen that the curved form of tip 52 provides a laterally wider structure within the SVC which is substantially wider than a single catheter body width due to the two (2) catheter body widths (66 and 68) in a lateral direction and the open space between downstream section 66 and upstream section 68. As illustrated, the curved tip 52 includes upstream section 68, distal section 64 and downstream section 66. In effect, by forming curved tip 52 with curved distal section 64, the lateral width or dimension of catheter 50 across curved tip 52 includes the lateral width of two (2) catheter bodies and the lateral width of the open space 70 between those two (2) catheter body sections 66 and 68. This lateral width is therefore at least twice the lateral width of a single catheter body depending on the size or lateral width of the open space 70 between the two sections. The selection of where to establish the lateral width across curved tip 52 will include at most the two catheter body sections and open space 70. The lateral width is determined in part by the size and curvature of section 64. The lateral width can be selectively established relative to the interior size of the SVC vein at that particular position so as to provide adequate reinforcement to the SVC vein wall. As noted, the curved shape of tip 52 also functions as a vein wall reinforcement so as to limit the amount of vein wall movement which might otherwise occur due to the suction force which is present at flow opening 58. A further contributing factor to prevent flow opening occluding, either partially or entirely, is the location and direction of flow opening 58. Since the flow opening 58 is in alignment with the body's natural blood flow pattern, essentially the entirety of the suction force is applied to pulling in "bad" blood and is not as available for acting on the SVC wall. Even if the SVC wall was inclined to be pulled inwardly, the structural reinforcement provided by the curved tip 52, limits any movement to the point that flow opening 58 is not occluded by the SVC wall. The curved tip 52 is formed such that opening 60 is laterally across from opening 58.

With further reference to the lateral width, it will be seen that the lateral width of the catheter body 51 upstream from opening 60 must accommodate both lumens 54 and 56. However, with the truncation of lumen 56 in order to create opening 60, the remaining "downstream" portion of the catheter body 51 only needs to accommodate lumen 54. Depending on the size and curvature of section 64, and depending on where the lateral width line is taken, the lateral width could include two (2) body widths of the portion downstream from opening 60. Alternative the lateral width could include one (1) width of the downstream portion (lumen 54) and one (1) width of the upstream portion (lumens 54 and 56). Each option would still likely include the lateral width of some portion of open space 70.

Figure 5:
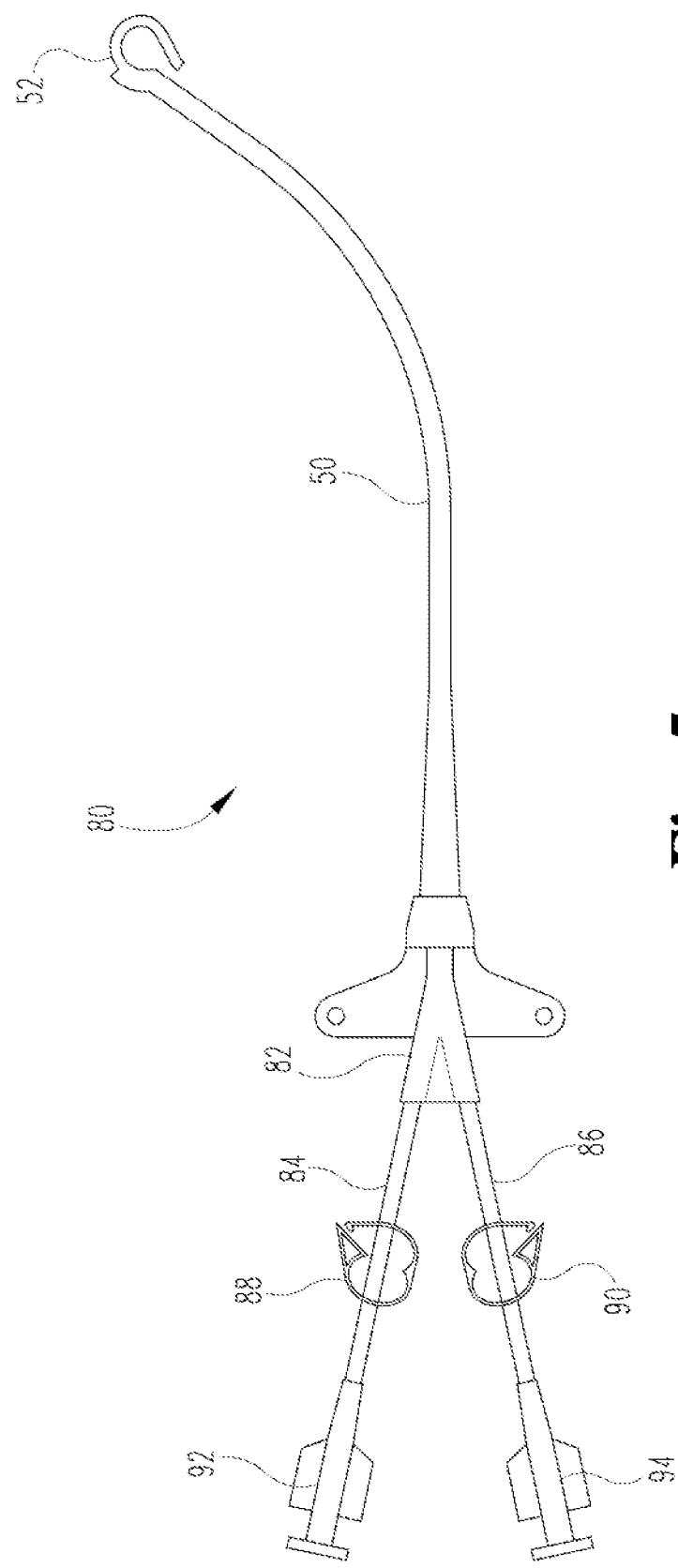
FIG. 5 is a diagrammatic view of a hemodialysis catheter system according to the exemplary embodiment.

Referring now to FIG. 5, a catheter system 80, including catheter 50, is illustrated. System 80 further includes catheter manifold 82, tubing sections 84 and 86, clamps 88 and 90 and connection hubs 92 and 94. Tubing section 84 connects hub 92 with lumen 54 via manifold 82. Tubing section 86 connects hub 94 with lumen 56 via manifold 82.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A hemodialysis catheter comprising:
   a catheter body having an elongate form with a proximal end and a distal end, said catheter body defining an arterial lumen and a venous lumen;
   said arterial lumen having an end which defines an arterial opening, said arterial opening being adapted to receive a flow of blood;
   said venous lumen having an end which defines a venous opening, said venous opening being adapted to deliver a flow of blood; and
   said catheter body includes a curved tip having a shape with an open space and which is constructed and arranged so as to position the arterial opening of said arterial lumen on one side of said open space and to position the venous opening of said venous lumen on an opposite side of said open space, said curved tip being adapted to be oriented in a vein with a natural flow of blood therethrough, such that said arterial opening opens in an upstream direction such that said flow of blood at the point of entering said arterial opening is in line with the natural flow of blood in said vein, flowing in substantially the same direction, said venous opening opens in a downstream direction such that said flow of blood at the point of exiting said venous opening is in line with the natural flow of blood in said vein, flowing in substantially the same direction.

2. The hemodialysis catheter of claim 1 wherein said curved tip has a curvature of substantially 180 degrees.

3. The hemodialysis catheter of claim 1 wherein said curved tip includes an upstream section, a downstream section and a curved section therebetween.

4. The hemodialysis catheter of claim 1 wherein said distal end is free of any sideports.

5. A hemodialysis catheter system comprising the hemodialysis catheter of claim 1 in combination with connection tubing, a manifold and clamps.

6. A method of physically reinforcing a vein in order to prevent occluding a flow opening of a hemodialysis catheter due to an in-flow suction force, said hemodialysis catheter including a first lumen with a distal in-flow flow opening and a second lumen with a proximal out-flow flow opening, said method comprising the following steps:
   a) forming a curved tip at a distal end of said hemodialysis catheter, said curved tip including an arterial lumen on one side of said curved tip and a venous lumen on an opposite side of said curved tip; and
   b) inserting said curved tip into a vein with a blood flow direction such that the in-flow flow opening is upstream from said out-flow flow opening, wherein said curved tip has a physical size and shape which provides a physical reinforcement structure against vein wall movement into an occluding position over said in-flow flow opening by positioning said arterial lumen against a first wall portion of said vein and said venous lumen against a second wall portion of said vein.

7. The method of claim 6 which further includes as part of the forming step, the step of using a forming wire to heat-set the curved tip material.

8. The method of claim 6 wherein the forming step creates a curved tip with a curvature of substantially 180 degrees.

9. The method of claim 6 wherein the method is free of any step of fabricating any sideports adjacent the in-flow flow opening.

10. A hemodialysis catheter having a proximal end and a distal end and comprising:
 a catheter body having a distal curved tip at said distal end, said catheter body defining an arterial lumen with a flow inlet opening and a venous lumen with a flow outlet opening; and
 said distal curved tip being constructed and arranged wherein, when in use in a vein with a natural flow of blood, the direction of the flow of blood at the point of entry into said flow inlet opening and the direction of the flow of blood at the point of exit from said flow outlet opening are flows in substantially the same direction and are flows which are in line with the natural flow of blood in the vein wherein said flow inlet opening faces in an upstream direction of said natural flow of blood and said flow outlet opening faces in a downstream direction of said natural flow of blood.

11. The hemodialysis catheter of claim 10 wherein said distal curved tip has a curvature of substantially 180 degrees.

12. The hemodialysis catheter of claim 10 wherein said distal curved tip includes an upstream section, a downstream section and a curved section therebetween.

13. The hemodialysis catheter of claim 10 wherein said distal curved tip defines an open space which is between two sections of said distal curved tip wherein said distal curved tip is adapted to provide physical reinforcement to a vein.

14. The hemodialysis catheter of claim 10 wherein said distal curved tip is free of any side ports, adjacent said flow inlet.

* * * * *